(12) United States Patent
Clyde et al.

(10) Patent No.: US 6,468,407 B2
(45) Date of Patent: Oct. 22, 2002

(54) NO$_X$ REDUCTION SENSOR COATING

(75) Inventors: Eric P. Clyde, Midland; Paul Kikuchi, Fenton; Richard F. Beckmeyer, Clarkston; William J. LaBarge, Bay City, all of MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/741,763

(22) Filed: Dec. 19, 2000

(65) Prior Publication Data

US 2002/0106307 A1 Aug. 8, 2002

(51) Int. Cl.$^7$ ............................................... G01N 27/26
(52) U.S. Cl. .................... 204/429; 204/421; 204/423; 204/424; 204/427; 204/428; 204/431; 204/432
(58) Field of Search ............................. 422/98, 90, 88, 422/83, 82.07, 95; 73/23.2; 204/421–429; 123/697; 438/49; 436/139; 338/34

(56) References Cited

U.S. PATENT DOCUMENTS

| | | | | |
|---|---|---|---|---|
| 4,428,909 A | * | 1/1984 | Yashiki et al. | 422/95 |
| 4,453,151 A | * | 6/1984 | Leary et al. | 338/34 |
| 4,601,914 A | * | 7/1986 | Barnes et al. | 438/49 |
| 4,944,273 A | | 7/1990 | Baresel et al. | |
| 5,296,196 A | * | 3/1994 | Takeshima | 422/98 |
| 5,346,679 A | | 9/1994 | Osaki et al. | |
| 5,490,490 A | * | 2/1996 | Weber et al. | 123/697 |
| 5,841,021 A | * | 11/1998 | De Castro et al. | 73/23.2 |
| 5,965,451 A | * | 10/1999 | Plog et al. | 436/139 |
| 6,033,641 A | | 3/2000 | Hall et al. | |
| 6,052,989 A | | 4/2000 | McCabe et al. | |
| 6,087,295 A | | 7/2000 | Kharas et al. | |
| 6,251,342 B1 | * | 6/2001 | Narula et al. | 422/82.07 |
| 6,325,979 B1 | * | 12/2001 | Hahn et al. | 422/88 |

FOREIGN PATENT DOCUMENTS

| | | |
|---|---|---|
| EP | 0062466 | 10/1982 |
| JP | 01227951 | 9/1989 |
| JP | 05045319 | 2/1993 |
| JP | 05087758 | 4/1993 |
| JP | 07080315 | 3/1995 |
| JP | 10274636 | 10/1998 |

* cited by examiner

Primary Examiner—Jill Warden
Assistant Examiner—Brian Sines
(74) Attorney, Agent, or Firm—Vincent A. Cichosz

(57) ABSTRACT

A sensor is disclosed that comprises an electrolyte disposed between and in intimate contact with a sensing electrode and a reference electrode. A protective coating is disposed on the protective layer adjacent to the sensing electrode. The protective coating comprises a mixture of a metal oxide, a zeolite, and an alumina. A method for making the sensor is also disclosed.

20 Claims, 1 Drawing Sheet

$NO_X$ REDUCTION SENSOR COATING

TECHNICAL FIELD

The present disclosure relates to exhaust sensors, and particularly to sensors with $NO_X$ reduction coatings.

BACKGROUND

The automotive industry has used exhaust gas sensors in automotive vehicles for many years to sense the composition of exhaust gases, namely, oxygen. For example, a sensor is used to determine the exhaust gas content for alteration and optimization of the air to fuel ratio (A/F) for combustion.

One type of sensor uses an ionically conductive solid electrolyte between porous electrodes. For oxygen, solid electrolyte sensors are used to measure oxygen activity differences between an unknown gas sample and a known gas sample. In the use of a sensor for automotive exhaust, the unknown gas is exhaust and the known gas, (i.e., reference gas), is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force ("emf") is developed between the electrodes according to the Nernst equation.

With the Nernst principle, chemical energy is converted into electromotive force. A gas sensor based upon this principle typically consists of an ionically conductive solid electrolyte material, a porous electrode with a porous protective overcoat exposed to exhaust gases ("exhaust gas electrode"), and a porous electrode exposed to a known gas' partial pressure ("reference electrode"). Sensors typically used in automotive applications use a yttrium stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right) \ln\left(\frac{P_{O_2}^{ref}}{P_{O_2}}\right)$$

where:

$E$ = electromotive force
$R$ = universal gas constant
$F$ = Faraday constant
$T$ = absolute temperature of the gas
$P_{O_2}^{ref}$ = oxygen partial pressure of the reference gas
$P_{O_2}$ = oxygen partial pressure of the exhaust gas Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating fuel-rich or fuel-lean, conditions without quantifying the actual air-to-fuel ratio of the exhaust mixture.

Oxygen sensors measure all of the oxygen present in the exhaust to make the correct determination when the oxygen content (air) exactly equals the hydrocarbon content (fuel). The oxygen sensor platinum electrode is very efficient at converting the hydrocarbons and carbon monoxide to form carbon dioxide and water. Unfortunately, the platinum electrode is unable to reduce the oxygen containing the species $NO_X$, with hydrocarbons, to form nitrogen, carbon dioxide and water.

A fuel can have a hydrocarbon content such that it takes 14.70 parts air (oxygen) to exactly combust 1.00 part fuel to form the products of carbon dioxide and water. Some of the oxygen may also be consumed in the reaction of nitrogen and oxygen to form nitrous/nitric oxides. Similarly, some of the oxygen may be consumed in the reaction of sulfur and oxygen to form sulfuric/sulfurous oxides. Nitrous/nitric oxides or sulfurous/sulfuric oxides will not react with hydrocarbons on a platinum electrode. Therefore, hydrocarbons are present and the sensor does not switch at the correct point. As a result, excess air is introduced until the hydrocarbon is reacted and the oxygen is detected.

In this case, instead of switching at 14.70 parts air to 1.00-part fuel, the sensor switches at 14.75 parts air to 1.00 part fuel. This is referred to as a "lean shift" because the switching point is shifted more lean than the true stoichiometric point. Operating an engine with a lean shifted sensor results in excess nitrogen oxides being released to the atmosphere since there are not enough hydrocarbons to reduce the nitrogen oxides in the catalytic converter. Since nitrogen oxides are the exhaust component responsible for the formation of "smog", it is desirable to correct the lean shift in the sensor.

One approach for treating nitrogen oxides in exhaust gases of engines operating under lean-burn conditions has been to incorporate $NO_X$ adsorbers in exhaust lines along with three way catalysts. Conventional exhaust systems contemplate any number of configurations, including for example, use of $NO_X$ adsorbers in the same canister along with three-way catalysts or use of a $NO_X$ adsorber in a separate can upstream of the three-way catalyst, among others. Rhodium is typically used in the industry to liberate oxygen from $NO_X$. However, rhodium affects the sensor signal such that the platinum-rhodium electrodes provide no net improvement in sensor control and often an increase in the emissions will result.

A second approach has been to alter the oxygen sensor in an attempt to correct the lean shift. A platinum-rhodium mixture has been used to form the electrodes. However, such a composition depresses the sensor performance to an unacceptable level. Rhodium or a mixture of platinum and rhodium has also been used to form a separate layer in between the sensing electrode and protective layer. However, the durability of the rhodium and the functionality of the sensor are not as good as desired when such a layer is included.

With current sensor and catalyst technology, exhaust emissions are reduced about 99.8%. An increase in the catalyst quantity does not improve efficiency. One way to eliminate a significant portion of the last 0.2% pollutant is to correct for the lean shifted sensor. Accordingly, there remains a need in the art for lean shift corrected sensor technology.

SUMMARY

The drawbacks and disadvantages of the prior art are overcome by a $NO_X$ reduction sensor coating.

A sensor is disclosed that comprises an electrolyte disposed between and in intimate contact with a sensing electrode and a reference electrode. A protective coating is disposed on the protective layer adjacent to the sensing electrode. The protective coating comprises a mixture of a metal oxide, a zeolite, and alumina.

A method for manufacturing a sensor is disclosed. The method comprises disposing an electrolyte between a sensing electrode and a reference electrode. A protective layer is disposed adjacent to the sensing electrode. A protective coating, which comprises a mixture of a metal oxide, a zeolite, and alumina is disposed in physical contact with the protective layer.

BRIEF DESCRIPTION OF THE DRAWINGS

Referring now to the FIGURE, which is meant to be exemplary, not limiting.

DESCRIPTION OF THE PREFERRED EMBODIMENT

Figure 1:
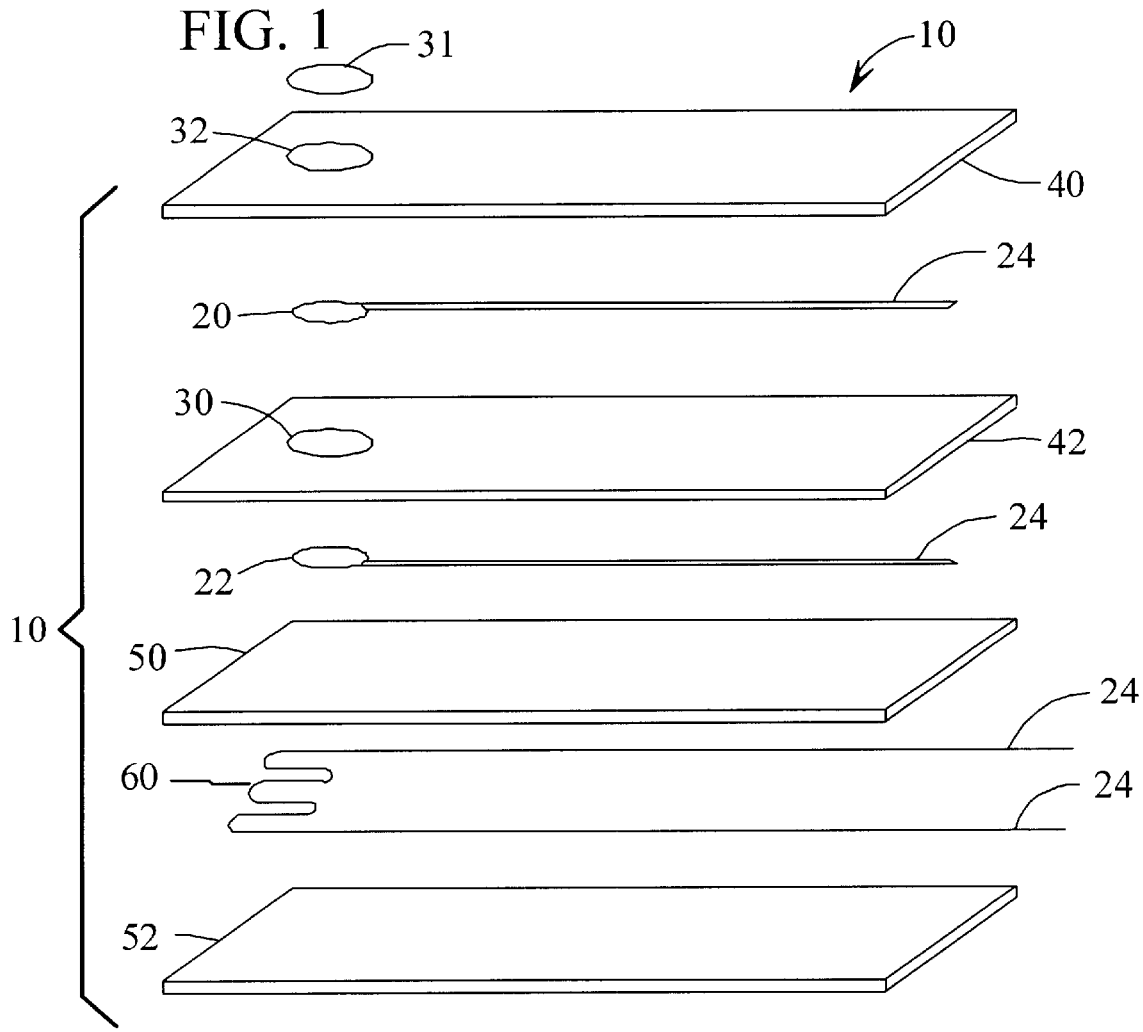
FIG. 1 is an expanded view of an oxygen sensor.

A lean shift corrected oxygen sensor, when used with a standard catalytic converter, can significantly reduce $NO_x$ emissions. A conventional oxygen sensor can be made into a lean shift corrected oxygen sensor by changing the composition of the protective coating. Instead of disposing a coating to protect the sensor from poisons, such as silicon, a NOx reactive coating (hereinafter NRC) can be disposed. A NRC for sensors, in particular oxygen sensors, is formed from a NOx catalyst composition. Although described in connection with an oxygen sensor, it is to be understood that the NRC coating can be employed with any type of oxygen sensor. Furthermore, while oxygen is the reference gas used in the description disclosed herein, it should be understood that other gases could be employed as a reference gas.

The sensor comprises a sensing electrode capable of sensing an exhaust gas, a reference electrode capable of sensing a reference gas, an electrolyte disposed between and in intimate contact with a first side of the sensing electrode and a first side of the reference electrode, with a first side of a protective layer disposed adjacent to the second side of the sensing electrode, and at least a portion of a second side of the protective layer having a NOx reactive coating.

Referring to FIG. 1, the sensor element 10 is illustrated. The exhaust gas (or outer) electrode 20 and the reference gas (or inner) electrode 22 are disposed on opposite sides of, and adjacent to, an electrolyte layer 30 creating an electrochemical cell (20/30/22). On the side of the exhaust gas electrode 20 opposite solid electrolyte 30 is an optional protective insulating layer 40 with a porous section 32 that enables fluid communication between the exhaust gas electrode 20 and the exhaust gas. A protective coating 31 can be disposed over the porous section 32. The electrolyte 30 and the porous section 32 can be disposed adjacent to, or as inserts within, layers 40, 42, respectively. Meanwhile, disposed on a side of the reference electrode 22 opposite electrolyte layer 30 is a heater 60. Typically disposed between the reference gas electrode 22 and the heater 60, as well as on a side of the heater 60 opposite the reference gas electrode 22, are one or more insulating layers 50, 52.

In addition to the above sensor components, conventional components can be employed, including, but not limited to, leads, contact pads, ground plane(s), support layer(s), additional electrochemical cell(s), and the like. The leads 24, which supply current to the heater and electrodes, are typically formed on the same layer as the heater/electrode to which they are in electrical communication and extend from the heater/electrode to the terminal end of the gas sensor where they are in electrical communication with the corresponding via (not shown) and appropriate contact pads (not shown).

Insulating layers 50, 52, and protective layer 40, provide structural integrity (e.g., protect various portions of the gas sensor from abrasion and/or vibration, and the like, and provide physical strength to the sensor), and physically separate and electrically isolate various components. The insulating layer(s), which can be formed using ceramic tape casting methods or other methods such as plasma spray deposition techniques, screen printing, stenciling and others conventionally used in the art, can each be up to about 200 microns thick or so, with a thickness of about 50 microns to about 200 microns preferred. Since the materials employed in the manufacture of gas sensors preferably comprise substantially similar coefficients of thermal expansion, shrinkage characteristics, and chemical compatibility in order to minimize, if not eliminate, delamination and other processing problems, the particular material, alloy or mixture chosen for the insulating and protective layers is dependent upon the specific electrolyte employed. Typically these insulating layers comprise a dielectric material such as alumina, and the like.

Disposed between the insulating layers 50, 52, is a heater 60 that is employed to maintain the sensor element at the desired operating temperature. Heater 60 can be any conventional heater capable of maintaining the sensor end at a sufficient temperature to facilitate the various electrochemical reactions therein. The heater 60, which is typically platinum, aluminum, palladium, and the like, as well as oxides, mixtures, and alloys comprising at least one of the foregoing metals, or any other conventional heater, is generally screen printed or otherwise disposed onto a substrate to a thickness of about 5 microns to about 50 microns.

Disposed on an opposite side of insulating layer 50 as heater 60 is the electrolyte 30. The electrolyte 30 can be solid or porous, can comprise the entire layer or a portion thereof, can be any material that is capable of permitting the electrochemical transfer of oxygen ions, should have an ionic/total conductivity ratio of approximately unity, and should be compatible with the environment in which the gas sensor will be utilized (e.g., up to about 1,000° C.). Possible electrolyte materials can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as combinations comprising at least one of the foregoing materials. For example, the electrolyte can be alumina and/or yttrium stabilized zirconia. Typically, the electrolyte, which can be formed via many conventional processes (e.g., die pressing, roll compaction, stenciling, screen printing, tape casting techniques, and the like), has a thickness of up to about 500 microns or so, with a thickness of about 25 microns to about 500 microns preferred, and a thickness of about 50 microns to about 200 microns especially preferred.

It should be noted that the electrolyte layer 30 and porous section 42 can comprise an entire layer or a portion thereof, e.g., they can form the layer (i.e., 42 and 40, respectively), be attached to the layer (porous section/electrolyte abutting dielectric material), or disposed in an opening in the layer (porous section/electrolyte can be an insert in an opening in a dielectric material layer). The latter arrangement eliminates the use of excess electrolyte and protective material, and reduces the size of gas sensor by eliminating layers. Any shape can be used for the electrolyte and porous section, with the size and geometry of the various inserts, and therefore the corresponding openings, being dependent upon the desired size and geometry of the adjacent electrodes. It is preferred that the openings, inserts, and electrodes have a substantially compatible geometry such that sufficient exhaust gas access to the electrode(s) is enabled and sufficient ionic transfer through the electrolyte is established.

The electrodes 20, 22, are disposed in ionic contact with the electrolyte layer 30. Conventional electrodes can comprise any catalyst capable of ionizing oxygen, including, but not limited to, materials such as platinum, palladium, osmium, rhodium, iridium, gold, ruthenium, zirconium, yttrium, cerium, calcium, aluminum, silicon, and the like, as well as oxides, mixtures, and alloys comprising at least one of the foregoing catalysts. As with the electrolyte, the electrodes 20, 22 can be formed using conventional techniques. Some possible techniques include sputtering, painting, chemical vapor deposition, screen-printing, and stenciling, among others. If a co-firing process is employed for the formation of the sensor, screen-printing the electrodes onto appropriate tapes is preferred due to simplicity, economy, and compatibility with the co-fired process. Electrode leads (24) and vias (not shown) are typically formed simultaneously with electrodes.

On at least the outer surface of the protective layer 40 is a NOx reactive coating (NRC) 31, as illustrated in FIG. 1. This NRC 31, which may optionally coat a portion or all of substrate layer 40 and/or support layer 52, is formed from a composition comprising a metal oxide and a support such as zeolite and alumina. Possible metal oxides comprise calcium oxide, strontium oxide, barium oxide, manganese oxides, tin oxides, copper oxides, cobalt oxides, lead oxides, aluminum oxide, silicon oxide, titanium oxide, zirconium oxides, lanthanum oxides as well as alloys and combinations comprising at least one of the foregoing metal oxides.

The preferred coating comprises a Y-type zeolite, whose molecules enclose cations of strontium, barium, a corresponding synthetic compound, and the like, as well as combinations comprising at least one of the foregoing cations. The Y-type zeolite may also contain additional stabilizers such as aluminum oxide and manganese oxide. A Y-type zeolite, having a silica to alumina ratio of less than 5 is preferred. The coating can comprise a metal oxide at about 1 weight percent (wt. %) to about 28 wt. %, a zeolite at about 50 wt. % to about 98 wt. % and aluminum oxide at about 1 wt. % to about 48 wt. %, with a metal oxide at about 10 wt. % to about 20 wt. %, a zeolite at about 50 wt. % to about 75 wt. %, and aluminum oxide at about 15 wt. % to about 40 wt. % preferred, and with a metal oxide at about 13 wt. % to about 15 wt. %, a zeolite at about 51 wt. % to about 61 wt. %, and aluminum oxide at about 24 wt. % to about 36 wt. % especially preferred. Preferably, the metal oxide utilized with the zeolite and aluminum oxide is barium oxide.

Although the NRC 31 can be applied to the porous section 32 of the protective layer 40 in a conventional fashion using techniques such as imbibing, spraying, spray coating, painting, dipping, spin coating, vapor deposition, and the like, dipping is preferred due to simplicity. For example, a solution, suspension, ink, paste, slurry, or the like is prepared by mixing barium-zeolite with a aluminum-zeolite in a solvent. Some possible solvents include water, benzoic acid, acetic acid, citric acid, and the like, as well as a combination comprising at least one of the foregoing solvents. Once the slurry is prepared, the slurry can then be applied to the desired area of the sensor. Typically the coating is applied at least to the porous section 32 of the protective layer 40, and optionally to the entire layer 40 and/or the support layer 52. The thickness of the protective coating 31 is based upon the ability to allow the passage of the exhaust gases to be sensed. Although a multi-layered coating can be employed, the protective coating is preferably a single layer having an overall thickness of up to about 200 microns ($\mu$m) or so, with a thickness of about 120 $\mu$m to about 160 $\mu$m preferred.

The first step in creating a NRC sensor comprising mixing the metal oxide and the zeolite. The solution created is then filtered, dried, and calcined (e.g., at a temperature of about 700° C. for about two hours). This metal oxide-zeolite powder can be mixed with ammonium aluminum hydrate to form a slurry. The sensor can then be dipped into the slurry, dried, and calcined (e.g., at a temperature of about 500° C. to about 700° C.) to create the NRC sensor.

A NRC sensor can be formed in accordance with the following examples.

EXAMPLE 1

A barium-zeolite powder can be prepared by mixing about 1,000 grams 13X zeolite and 2 liters saturated barium nitrate solution in a container. The reaction initially is exothermic and the temperature is maintained at about 80° C. for at least about 2 hours. The material is then filtered and washed. The filtered material is dried and calcined to about 700° C. for about 2 hours. This process is repeated three times. The material is then analyzed to determine that it comprises the desired amount of metal oxide; e.g., about 18 wt. % and to about 28 wt. % barium.

After creating the metal oxide-zeolite powder, the composition for forming the protective coating is created. About 1,000 grams of barium-zeolite powder, about 80 grams of 25 wt. % ammonium aluminum hydrate, and about 1,000 grams of water are mixed in a container to form a slurry. A conical sensor can be dipped into the stirred slurry. The sensor is then dried and calcined at about 500° C.

EXAMPLE 2

First, a barium aluminum powder is prepared. About 1,000 grams Condea Vista SCFA-100 gamma alumina and about 640 grams of 3.8 wt. % barium 2-ethyl hexanoate in toluene are mixed in a container. The mixture is dried and calcined to about 700° C. for about 2 hours. 280 grams of barium-alumina powder is then mixed with about 720 grams of barium-zeolite powder, 80 grams of 25 wt. % ammonium aluminum hydrate, and 1,000 grams of water in a container to form a slurry. A conical sensor can be dipped into the stirred slurry. The sensor is then dried and calcined at about 500° C.

EXAMPLE 3

280 grams of the barium-alumina powder is then mixed with about 620 grams of the barium-zeolite powder, 80 grams of manganese dioxide, 80 grams of 25 wt. % ammonium aluminum hydrate, and 1,000 grams of water in a container to form a slurry. A conical sensor can be dipped into the stirred slurry. The sensor is then dried and calcined at about 500° C.

EXAMPLE 4

About 540 grams of the barium-zeolite powder, 280 grams of the barium-alumina powder, 80 grams of manganese dioxide, 80 grams of titanium dioxide, 80 grams of 25 wt. % ammonium aluminum hydrate, and 1,000 grams of water are mixed in a container to form a slurry. A conical sensor can be dipped into the stirred slurry. The sensor is then dried and calcined at about 500° C.

EXAMPLE 5

A lead-alumina powder is formed. About 1,000 grams Condea Vista SCFA- 100 gamma alumina and about 360 grams of 7.2 wt. % lead 2-ethyl hexanoate in toluene are mixed in a container. The mixture is dried and calcined to about 500° C. for about 2 hours. 280 grams of the lead-alumina powder is mixed with 440 grams of barium-zeolite powder, 280 grams of the barium-alumina powder, 80 grams of 25 wt. % ammonium aluminum hydrate, and 1,000 grams of water in a container to form a slurry. A conical sensor can be dipped into the stirred slurry. The sensor is then dried and calcined at about 500° C.

Tailpipe emissions with existing sensor and catalyst technology may reduce $NO_X$ to about 0.08 mg/mile, while a NRC sensor may reduce emissions to about 0.04 mg/mile which meets and is lower than the federal standards by about 40%. This decrease to about 0.04 mg/mile translates into about a 50% reduction in the amount of NOx released. Consequently, employing the NRC enables a decrease in NOX emissions from an emission level obtained with conventional sensors by greater than about 25%, with greater than about 35% preferred, and about 50% or so especially preferred.

By disposing the protective coating comprising a metal oxide, a zeolite, and alumina on a sensor, a conventional oxygen sensor can be made into a lean shift corrected oxygen sensor. A lean shift corrected oxygen sensor, when used with a standard catalytic converter, can significantly reduce $NO_X$ emissions. The addition of this protective coating to a sensor enables a vehicle to meet Federal standards, and may lead to a reduction in the volume of current catalyst used by about 30% or greater. The NRC is cost effective and does not affect the sensor's performance, yet improves the exhaust system emissions levels While preferred embodiments have been shown and described, various modifications and substitutions may be made thereto without departing from the spirit and scope of the invention. Accordingly, it is to be understood that the present invention has been described by way of illustration, and not limitation.

What is claimed is:

1. A sensor, comprising:
   an electrolyte disposed between and in intimate contact with a sensing electrode and a reference electrode; and
   a protective layer disposed adjacent to said sensing electrode, wherein said protective layer has a protective coating comprising a mixture of a metal oxide, a zeolite, and alumina.

2. The sensor of claim 1, wherein said protective coating comprises about 1 wt. % to about 28 wt. % metal oxide, about 50 wt. % to about 98 wt. % zeolite, and about 1 wt. % to about 48 wt. % alumina.

3. The sensor of claim 2, wherein said protective coating comprises about 10 wt. % to about 20 wt. % metal oxide, about 50 wt. % to about 75 wt. % zeolite, and about 15 wt. % to about 40 wt. % alumina.

4. The sensor of claim 3, wherein said protective coating comprises about 13 wt. % to about 15 wt. % metal oxide, about 51 wt. % to about 61 wt. % zeolite, and about 24 wt. % to about 36 wt. % alumina.

5. The sensor of claim 1, wherein said metal oxide comprises calcium oxide, strontium oxide, barium oxide, manganese oxide, tin oxide, copper oxide, cobalt oxide, lead oxide, aluminum oxide, silicon oxide, titanium oxide, zeolites, zirconium oxide, lanthanum oxide, as well as alloys and combinations comprising at least one of the foregoing metal oxides.

6. The sensor of claim 1, wherein said metal oxide is barium oxide.

7. The sensor of claim 1, wherein said zeolite is a Y-type zeolite, whose molecules enclose cations of strontium, barium, or a corresponding synthetic compound, as well as combinations comprising at least one of the foregoing cations.

8. The sensor of claim 1, wherein said protective coating has a thickness of up to about 200 $\mu$m.

9. The sensor of claim 8, wherein said protective coating has a thickness of about 120 $\mu$m to about 160 $\mu$m.

10. A method for manufacturing a sensor, comprising:
    disposing an electrolyte between a sensing electrode and a reference electrode;
    disposing a protective layer adjacent to said sensing electrode; and
    disposing a protective coating comprising a mixture of a metal oxide, a zeolite, and alumina in physical contact with said protective layer.

11. The method of claim 10, wherein said protective coating comprises about 1 wt. % to about 28 wt. % metal oxide, about 50 wt. % to about 98 wt. % zeolite, and about 1 wt. % to about 48 wt. % alumina.

12. The method of claim 11, wherein said protective coating comprises about 10 wt. % to about 20 wt. % metal oxide, about 50 wt. % to about 75 wt. % zeolite, and about 15 wt. % to about 40 wt. % alumina.

13. The method of claim 12, wherein said protective coating comprises about 13 wt. % to about 15 wt. % metal oxide, about 51 wt. % to about 61 wt. % zeolite, and about 24 wt. % to about 36 wt. % alumina.

14. The method of claim 10, wherein said metal oxide comprises calcium oxide, strontium oxide, barium oxide, manganese oxide, tin oxide, copper oxide, cobalt oxide, lead oxide, aluminum oxide, silicon oxide, titanium oxide, zeolites, zirconium oxide, lanthanum oxide, as well as alloys and combinations comprising at least one of the foregoing metal oxides.

15. The method of claim 10, wherein said metal oxide is barium oxide.

16. The method of claim 10, wherein said zeolite is a Y-type zeolite, whose molecules enclose cations of strontium, barium, or a corresponding synthetic compound, as well as combinations comprising at least one of the foregoing cations.

17. The method of claim 10, wherein said protective coating has a thickness of up to about 200 $\mu$m.

18. The method of claim 17, wherein said protective coating has a thickness of about 120 $\mu$m to about 160 $\mu$m.

19. The sensor of claim 5, wherein said metal oxide comprises calcium oxide, strontium oxide, barium oxide, manganese oxide, tin oxide, copper oxide, cobalt oxide, lead oxide, silicon oxide, titanium oxide, zeolites, zirconium oxide, lanthanum oxide, as well as alloys and combinations comprising at least one of the foregoing metal oxides.

20. The method of claim 14, wherein said metal oxide comprises calcium oxide, strontium oxide, barium oxide, manganese oxide, tin oxide, copper oxide, cobalt oxide, lead oxide, silicon oxide, titanium oxide, zeolites, zirconium oxide, lanthanum oxide, as well as alloys and combinations comprising at least one of the foregoing metal oxides.

* * * * *